United States Patent
Mesallum (10) Patent No.: US 9,636,443 B2
(45) Date of Patent: May 2, 2017

(54) SYSTEM FOR PRODUCING CONTINUOUS MECHANICAL ENERGY TO TREAT HEART FAILURE WITHOUT THE USE OF EXTERNAL ENERGY SOURCE

(71) Applicant: BRAVO BIOMED, INC., Rockland, MA (US)

(72) Inventor: Sameh Mesallum, Boston, MA (US)

(73) Assignee: BRAVO BIOMED, INC., Rockland, MA (US)

( * ) Notice: Subject to any disclaimer, the term of this patent is extended or adjusted under 35 U.S.C. 154(b) by 0 days.

(21) Appl. No.: 14/722,507

(22) Filed: May 27, 2015

(65) Prior Publication Data

US 2016/0106900 A1    Apr. 21, 2016

Related U.S. Application Data

(60) Provisional application No. 62/005,189, filed on May 30, 2014.

(51) Int. Cl.
    *A61M 1/12*     (2006.01)
    *A61M 1/10*     (2006.01)
    *A61N 1/378*     (2006.01)

(52) U.S. Cl.
    CPC .......... *A61M 1/127* (2013.01); *A61M 1/1003* (2014.02); *A61M 1/106* (2013.01); *A61M 1/1067* (2013.01); *A61M 1/122* (2014.02); *A61N 1/3785* (2013.01)

(58) Field of Classification Search
    CPC ........................... A61M 1/1003; A61M 1/127
    See application file for complete search history.

(56) References Cited

U.S. PATENT DOCUMENTS

| | | | | |
|---|---|---|---|---|
| 2,812,716 A * | 11/1957 | Gray | ..................... | F04B 43/086 128/DIG. 3 |
| 3,449,767 A * | 6/1969 | Bolie | ..................... | A61M 1/106 128/899 |
| 3,543,752 A * | 12/1970 | Hesse | ................. | A61M 1/3626 222/52 |
| 4,014,318 A * | 3/1977 | Dockum | ............ | A61M 1/1053 137/527 |
| 4,465,063 A * | 8/1984 | Nielsen | ................. | A61B 5/026 600/16 |
| 4,553,532 A * | 11/1985 | Bohls | ................. | A61M 1/1037 417/412 |
| 4,957,477 A * | 9/1990 | Lundback | ........... | A61M 1/1068 600/16 |
| 5,006,104 A * | 4/1991 | Smith | ..................... | F04B 43/06 417/395 |

(Continued)

*Primary Examiner* — Kennedy Schaetzle
(74) *Attorney, Agent, or Firm* — Lando & Anastasi, LLP (57) ABSTRACT

Described are aspects and embodiments directed to systems for tapping into the breathing system to generate pressure in a sustained space with pulsating frequency to aid the pumping functions of cardiac muscle. In some embodiments, the generated energy can also be transferred to other forms of energy (e.g., electricity to power certain devices (e.g., pacemaker batteries). In further embodiments, the system utilizes air entrapment in a closed space to generate mechanical force with valves and timed release frequency to control power generation and mechanical movements that assist blood flow.

16 Claims, 7 Drawing Sheets

(56) References Cited

U.S. PATENT DOCUMENTS

| | | | | |
|---|---|---|---|---|
| 5,169,381 A | * | 12/1992 | Snyders | A61M 1/1068 600/16 |
| 5,372,573 A | * | 12/1994 | Habib | A61M 1/1062 600/16 |
| 5,383,839 A | * | 1/1995 | Bohls | A61M 1/1037 600/16 |
| 5,813,410 A | * | 9/1998 | Levin | A61F 2/042 128/897 |
| 6,030,336 A | * | 2/2000 | Franchi | A61M 1/106 600/16 |
| 6,793,642 B2 | * | 9/2004 | Connelly | A61B 5/150229 422/44 |
| 2004/0152945 A1 | * | 8/2004 | Kantrowitz | A61M 1/1072 600/18 |
| 2006/0183963 A1 | * | 8/2006 | Weizman | A61M 1/1037 600/16 |
| 2008/0183286 A1 | * | 7/2008 | Vaska | A61M 1/1037 623/3.12 |
| 2016/0051806 A1 | * | 2/2016 | Goldsmith | A61N 1/00 604/21 |

* cited by examiner

SYSTEM FOR PRODUCING CONTINUOUS MECHANICAL ENERGY TO TREAT HEART FAILURE WITHOUT THE USE OF EXTERNAL ENERGY SOURCE

RELATED APPLICATIONS

This application priority under 35 U.S.C. §119(e) to U.S. Provisional Patent Application Ser. No. 62/005,189 entitled "SYSTEM FOR PRODUCING CONTINUOUS MECHANICAL ENERGY TO TREAT HEART FAILURE WITHOUT THE USE OF EXTERNAL ENERGY SOURCE," filed May 30, 2014, which application is incorporated herein by reference in its entirety.

BACKGROUND

Various conventional devices exist to help manage patient health. In particular, many devices with internal and external components exist to manage heart problems associated with any heart condition. In one example, a patient may be implanted with a ventricular assist device (VAD), which is a mechanical pump that is used to support heart function and blood flow in people who have weakened hearts. A VAD device takes blood from a lower chamber of the heart and helps pump it to the body and vital organs, just as a healthy heart would. Conventional pump assist devices require power sources, often external, and may also require control units that may be external to the patient.

SUMMARY OF THE INVENTION

It is realized that current heart assist devices require external power sources that are subject to failure and/or require replacement. Stated broadly various aspects and embodiments are directed to heart assist devices configured to generate mechanical force to assist heart functions. In some embodiments, the heart assist device is configured to harness energy generated by other bodily functions (e.g., respiration) and convert that energy into mechanical work that assists blood flow. Various embodiments relate to the field of heart assist devices used to treat heart failure. Current systems use external power sources and eventually fail to sustain mechanical pumping action. Various embodiments describe a system that generates mechanical force to assist blood pumping from the heart without any external energy source.

According to one embodiment, the system uses body muscle contraction in the creation and maintenance of pumping action by the heart. In some examples, muscle contractions outside of the heart can be converted into mechanical force applied to the heart or blood vessels proximate to the heart to facilitate blood flow. For example, muscles that work in autonomic fashion without the need of conscious control include muscles that regulate breathing (e.g., the diaphragm). Such autonomic muscles can be used to capture and supply mechanical force, which can be delivered to assist in blood pumping by the heart.

According to one embodiment, in case of heart muscle failure the breathing muscle contractions can be used to generate mechanical force to assist in blood pumping in an autonomic manner similar to the ordinary function of the heart muscle. Due to close relationship in the physiology and mechanisms of the contraction of the heart muscle and the breathing muscles, the latter is able to provide synchronous energy that matches body need. For example, in case of a person at rest or sleeping, the pumping demands on the heart muscle are low, which are matched by the demands on breathing musculature and a slow breathing frequency.

Further, in the case of stress (physical or psychological) the rate of breathing frequency increases and can be used to match the increased pumping demands on the heart muscle. The natural synchronization between blood demand and breathing demand can be used to secure enough increased energy production in case of increased demands on the heart muscle. According to some aspects, the energy produced by the breathing muscle is significant. For example in cases of tension pneumothorax, the air trapped in the thoracic cavity is under very high pressure where the pressure increases with each breath or inspiration. In some examples, the amount of pressure created in such conditions can exceed the high intra-cardiac pressure of the left ventricle and can lead to heart collapse and death. It is realized that this pressure and/or mechanical force can be utilized in a non-harmful way to produce an autonomic pump. According to some embodiments, the autonomic pump can be implemented without any need for an external power source.

According to one aspect, an implantable heart assist system is provided. The system comprises at least one an air capture inlet, a pressure chamber, and an actuator operative responsive to air pressure in the pressure chamber, wherein the actuator is positioned such that activation of the actuator compresses an adjacent blood vessel and forces blood flow. According to one embodiment, the system further comprises one way flow valves disposed in the air capture inlet.

According to one embodiment, the at least one air capture inlets are connected to an airway of a person. According to one embodiment, the at least one air captured inlet comprises tapping tubing mated to at least one internal breathing passage of a patient at a first end and connected to the pressure chamber at a second end. According to one embodiment, the tapping tubing further comprises one way flow valves disposed in the tapping tubing. According to one embodiment, the at least one air capture inlet permits air flow responsive to breathing by the person. According to one embodiment, the pressure chamber is connected to the at least one air capture inlet, and receives air flow from the at least one air capture inlet.

According to one embodiment, the pressure chamber further comprises a releasably closed air outlet. According to one embodiment, the releasably closed air outlet is constructed and arranged such that the air outlet opens responsive to a threshold pressure or air volume. According to one embodiment, the releasably closed air outlet is connected to the actuator. According to one embodiment, the actuator is operated responsive to opening the releasably closed air outlet. According to one embodiment, the actuator further comprises a plurality of compression chambers. According to one embodiment, the plurality of compression chambers are constructed and arranged to sequentially actuate and compress an adjacent blood vessel. According to one embodiment, the respective one of the plurality of compression chambers includes a release valve connected to an adjacent one of the plurality of compression chambers.

According to one embodiment, the release value is constructed and arranged to be covered when the respective one of the plurality of compressions chambers is in a non-actuated state, and wherein the release valve is exposed responsive to actuation of the respective one of the plurality of compression chambers. According to one embodiment, the actuator further comprises a piston, and the system further comprises a flywheel connected to the piston. According to one embodiment, the flywheel is positioned to compress an adjacent blood vessel responsive to rotation.

According to one embodiment, the flywheel includes at least one concave portion such that upon rotation the concave portion releases the compression on the adjacent blood vessel.

Still other aspects, embodiments and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Any embodiment disclosed herein may be combined with any other embodiment. References to "an embodiment," "an example," "some embodiments," "some examples," "an alternate embodiment," "various embodiments," "one embodiment," "at least one embodiment," "this and other embodiments" or the like are not necessarily mutually exclusive and are intended to indicate that a particular feature, structure, or characteristic described in connection with the embodiment may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. Where technical features in the figures, detailed description or any claim are followed by reference signs, the reference signs have been included for the sole purpose of increasing the intelligibility of the figures, detailed description, and claims. Accordingly, neither the reference signs nor their absence are intended to have any limiting effect on the scope of any claim elements. In the figures, each identical or nearly identical component that is illustrated in various figures is represented by a like numeral. For purposes of clarity, not every component may be labeled in every figure. The figures are provided for the purposes of illustration and explanation and are not intended as a definition of the limits of the invention. In the figures:

DETAILED DESCRIPTION

Stated broadly various aspects and embodiments are directed to systems for tapping into the breathing system to generate pressure in a sustained space with pulsating frequency to aid the pumping of cardiac muscle. In some embodiments, the generated energy can also be transferred to other forms of energy (e.g., electricity to power certain devices (e.g., pacemaker batteries). In further embodiments, the system utilizes air entrapment in a closed space to generate mechanical force with valves and timed release frequency to control power generation and mechanical movements.

According to one embodiment, the system can be extracorporeal, but in other embodiments, the system elements are contained within a body cavity (e.g. the thorax or the abdominal cavity). In some embodiments, the system does not affect the amount of air essential for oxygen exchange inside the lung alveoli but it adds a small amount of effort of breathing to achieve TLC (total lung capacity). For patients with the heat assist system, special training regarding breathing may be required. For example, breathing techniques can be taught to patients that emphasize the importance of diaphragmatic contraction as well as fully engaging accessory muscles of breathing contraction.

In some embodiments, the pressure generated by the system can be volume release controlled or pressure release controlled. According to one example, the system can include one or more volume release valves that maintain an outlet in a closed position until a volume is reached, opening the outlet and releasing the stored air/pressure as mechanical energy. In another example, one or more pressure release valves can be connected to an outlet that remains closed until a threshold pressure is released through the outlet. In some examples, the outlet is connected to a piston that is driven into a blood vessel. The pressure from the piston can be applied to assist blood flow through the vessel.

In further embodiments, air can be contained in one pressure chamber or in more than one chamber (e.g., in a series of sequential chambers to produce increasing or decreasing pressure pulse wave (crescendo or decrescendo)). The direction of the pressure pulse can be configured to generate force in the direction of normal blood flow by use of valves inside vascular compartments (e.g., where naturally occurring valves prevent backward flow). In another example, the system can be implanted with unidirectional flow valves in blood vessels subject to the applied force. In further implementations, the sequential application of force by a series of pistons can be used to affect the vascular compartments from outside the blood vessel and ensure blood flow in a normal direction.

According to some embodiments, the heart assist system uses small tubing connected to a large bore airway (e.g., trachea as main bronchi (right or left or both) for collecting air during inspiration. The air collected is entrapped in a contained space (e.g., pressure chamber) which can include one-way valves that accept air movement into the inside of the pressure chamber but prevent release of the air pressure, except under controlled conditions. With each breath, more air is directed into the pressure chamber increasing air pressure. Once the pressure inside the chamber reaches a threshold level, the pressure is released to generate a mechanical force. In some embodiments, the air pressure is applied to pushing a piston or actuator. The piston and/or actuator compress a target blood vessel resulting in increased pressure inside the target blood vessel assisting normal blood flow. In some alternative embodiments, the piston or actuator can be used to rotate a wheel (e.g., by a mechanism similar to crank shaft movement). The rotation of the wheel can be used to compress the target blood vessel increasing pressure inside the vessel to assist in normal blood flow. In some alternatives, the rotation of the wheel can be used to generate electricity, which can be used to deliver power to other heart and/or blood flow management devices (e.g., pacemaker devices).

In some embodiments, air pressure is released from the pressure chamber at a pre-assigned pressure level (and, for example, not completely emptying the pressure chamber to help in building pressure for the upcoming or next pressure cycle). According to various aspects and embodiments, the cycle of pressure generation and utilization can be completely autonomous and does not need any volitional control by patient.

Examples of the methods, devices, and systems discussed herein are not limited in application to the details of construction and the arrangement of components set forth in the following description or illustrated in the accompanying drawings. The methods and systems are capable of implementation in other embodiments and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples, and are combinable and combined in other embodiments.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Figure 1:
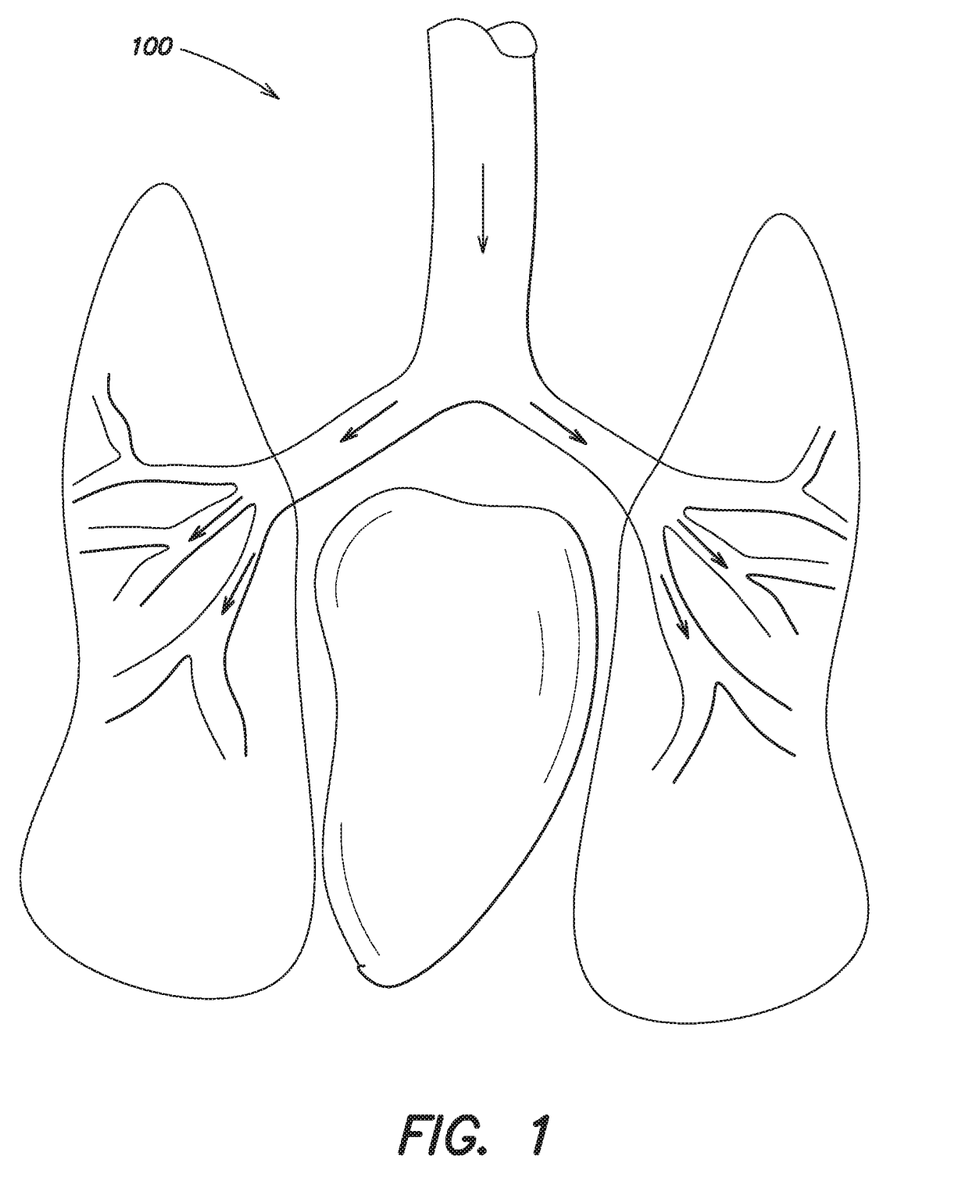
FIG. 1 is a partially transparent view of a right lung, heart and left lung.
Figure 2:
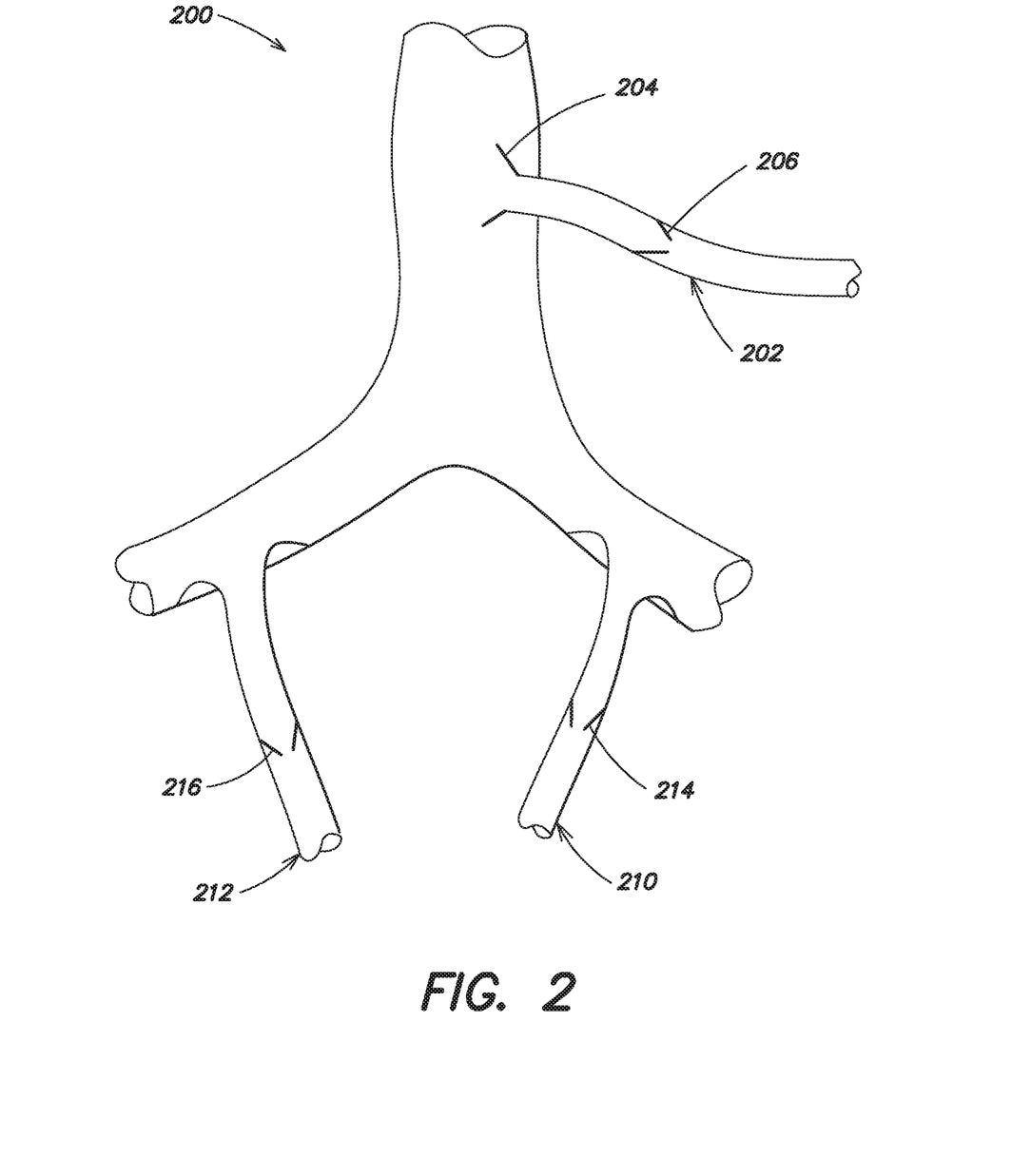
FIG. 2 is a partially transparent view of a trachea, right bronchus and/or left bronchus air.

FIG. 1 is a partially transparent view 100 of a right lung, heart and left lung. FIG. 2 is a partially transparent view 200 of a trachea, right bronchus, and left bronchus. A tapping tube or vessel 202 captures air from the trachea. In some embodiments, the tapping tube can be constructed from known catheter materials, including for example, plastic, rubber, and/or synthetic surgical material. In some embodiments, the tapping tube 202 includes one or more one way valves 204 and 206. As a person breaths, the increase air pressure in the trachea forces air through the tapping tube 202 and one way valves 204-206. The air forced through tapping tube 202 is collected in a pressure chamber (not shown). Various embodiments of a heart assist system can include multiple tapping tubes (e.g., 210 and 212). Each tapping tube can include one-way valves (e.g., 214-216) that capture air flow into respective pressure chambers.

Figure 3:
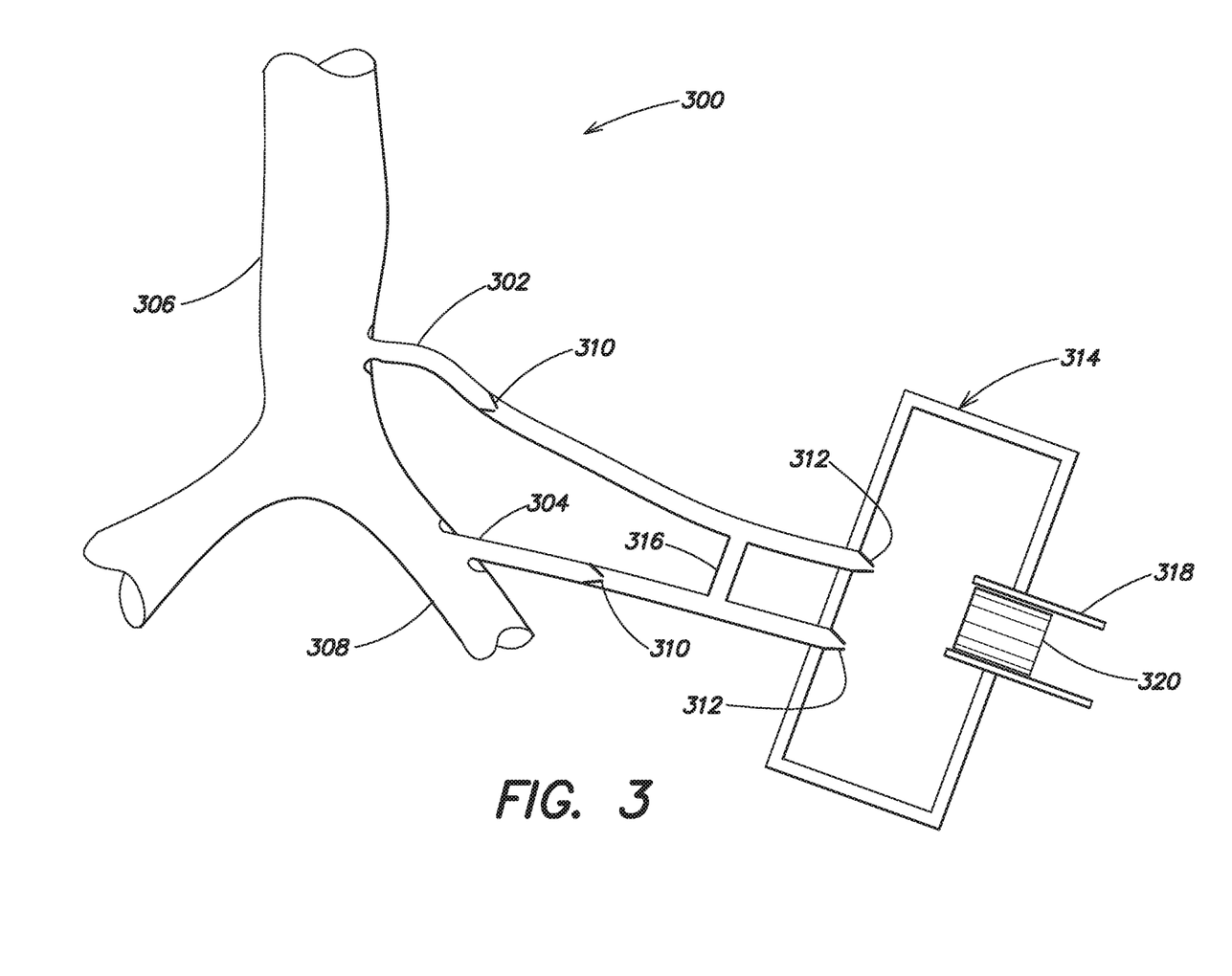
FIG. 3 is a partially transparent view of one embodiment of tapping tubes connected to air pressure bag.

FIG. 3 is a partially transparent view 300 of one embodiment of a heart assist system. At 302 and 304 tapping tubes capture air flow from the trachea 306 and/or the bronchus 308 (e.g., right or left). One way valves at 310 and 312 mange air flow so that air flows into a pressure chamber 314. At least some of the one way valves (e.g., 312) can be positioned at one or more air inlets (e.g., of the pressure chamber 314). In some embodiments, the tapping tubes can be connected (e.g., at 316) to deliver air from the trachea or bronchus to the pressure chamber 314. According to one embodiment, the pressure camber 314 is constructed with an air outlet 318 and piston 320. The air outlet 318 can include pressure and/or volume controls. For example, the outlet 318 can include a pressure relief valve that opens in response to a threshold pressure. In another example, the outlet can include a volume release valve that opens in response to a threshold air volume in the pressure chamber 314. In response to opening the outlet, air flow drives the piston 318. The piston can be positioned to compress a blood vessel (not shown) to assist blood flow.

In some embodiments, the outlet may include a return vessel or tapping tube that allows air flow back into a patient's airway. The return vessel may be blocked by the piston such that only when the piston is fully deployed is the return exposed. The return vessel can include one way valves that ensure pressure can only be released. In further embodiments, the return vessel may be directed back to the pressure chamber to facilitate a next piston deployment. And in yet other embodiments, the return vessel can be connected to the pressure chamber and the patient's airway. In some examples, the one way valves in the return vessels are constructed so that a greater mechanical force is required to overcome the valve in the return vessel connected to the patient's airway than the valves connected to the pressure chamber. Such a configuration can facilitate refilling of the pressure chamber and facilitate management of air volume in the system.

Figure 4A:
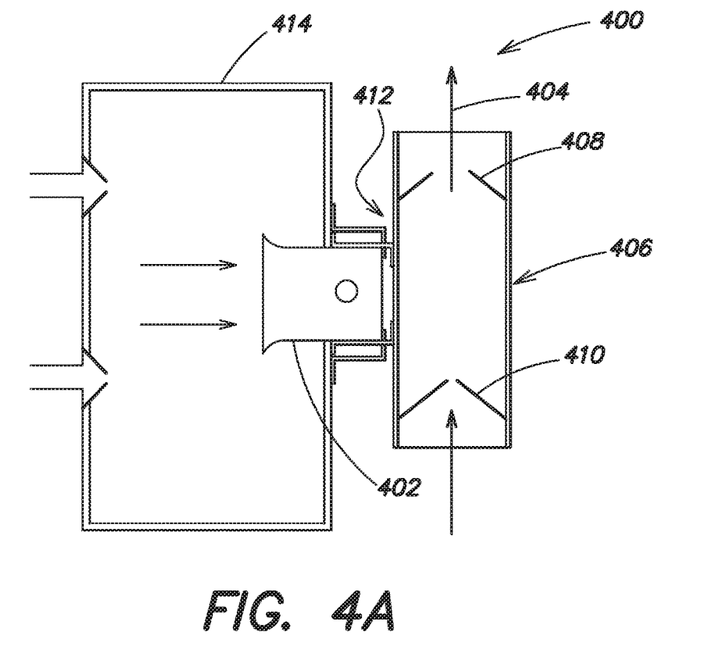
FIGS. 4A-B are partially transparent views of one embodiment of a piston deployed in pulses causing blood to move in one direction by means of one way valves.
Figure 4B:
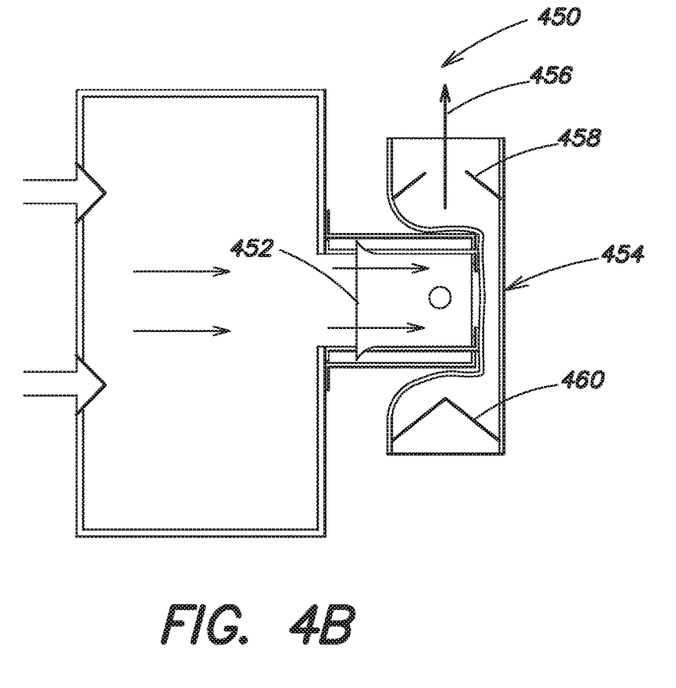

Shown in FIG. 4A is a partially transparent view 400 of a piston 402 deployed in pulses to assist blood flow in the normal flow direction (e.g., arrow 404). According to one embodiment, the piston 402 acts on a vascular compartment 406. The position of the assist system and/or the piston can be selected to act on an area where natural body valves exist to prevent improperly directed blood flow. In another example, the heart assist system can include implantable vascular compartments (e.g., 406). The vascular compartment can include one way valves 408-410 that do not impede normal flow but prevent blood flow in an opposite direction. As the vascular compartment is compressed the one way valves ensure the increased pressure propels blood flow in the normal direction (e.g., 404). The piston 402 can be controlled by a holding element 412. The holding element can include a rigid but releasable retainer. The releasable retainer holds the piston in place until, for example, a pressure threshold is reached in the pressure chamber 414. In another example, the releasable retaining element can be responsive to air volume, allowing the piston to advance responsive to a threshold volume of air. In some embodiments, the holding element 412 can be constructed and arranged to force the piston 402 into an non-deployed position. In other embodiments, the piston 402 is constructed and arranged to be biased to a non-deployed position and the piston 402 is configured to return to rest once the increase air pressure is released. In yet other embodiments, the FIG. 4B is a partially transparent view 450 of a piston 452 is a deployed position. In the deployed position, piston 452 compresses a vascular compartment 454. The vascular compartment can include one way valves 458-460 that direct blood flow only in the normal direction for blood flow. According to some embodiments, the air pressure increases in the pressure chamber until a triggering volume or pressure is reached, activating the piston and forcing blood flow in response to compression of the vascular compartment (e.g., a blood vessel). As a person breathes, air pressure will periodically reach the threshold volume or pressure, triggering the piston into a series of pulses that force blood flow assisting the normal operation of the heart.

Figure 5:
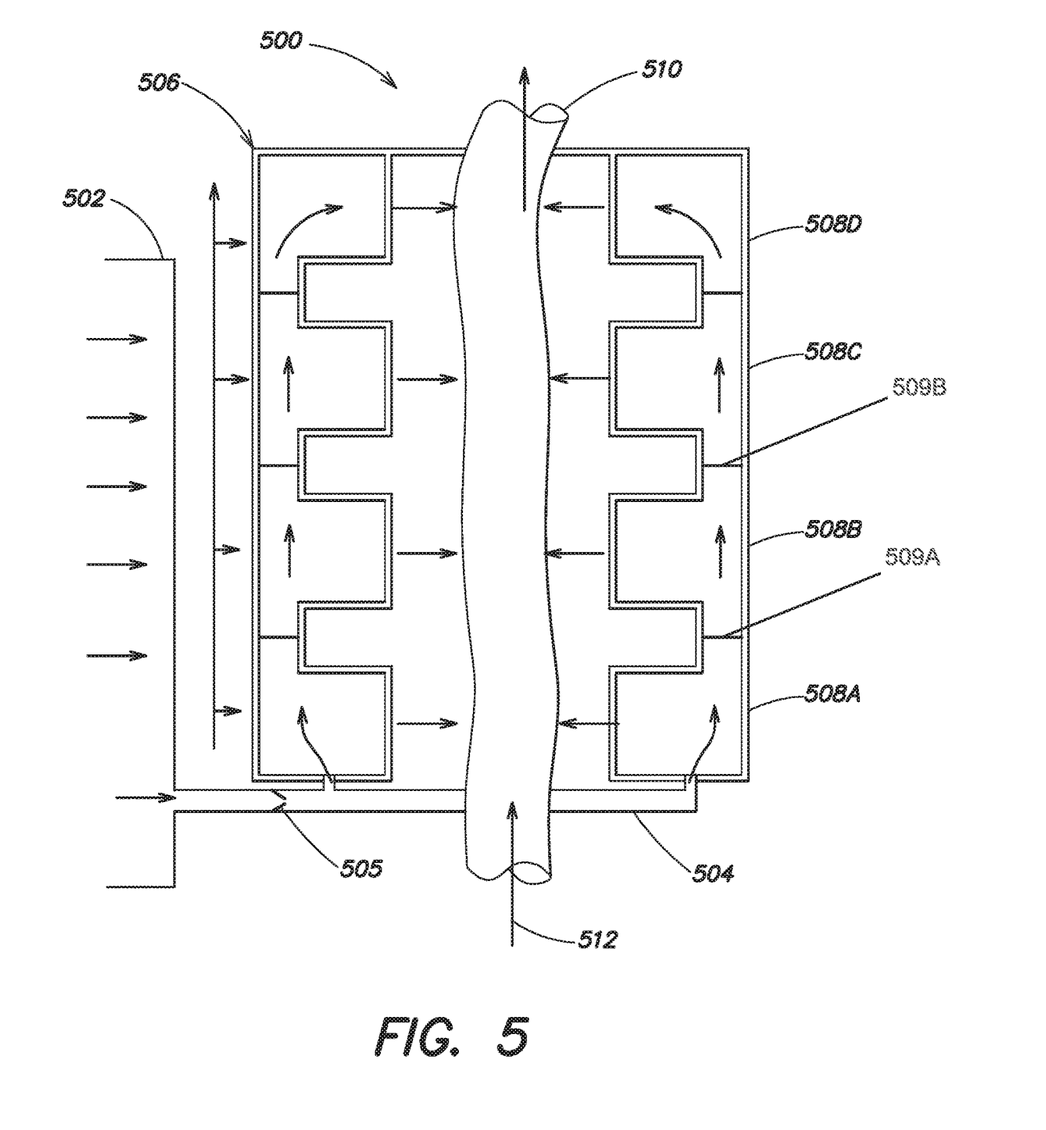
FIG. 5 is a partially transparent view of one embodiment of air pressure bag outlet connected to sequential air pressure chamber.

FIG. 5 is a partially transparent view 500 of a pressure chamber 502 and outlet 504 connected to sequential compression chamber 506. The air flow from the outlet can be managed by one way flow valves (e.g., at 505). Additionally, the outlet can include pressure and/or volume controls, that maintain the outlet 504 in a closed configuration until a threshold pressure and/or volume is obtained. According to one embodiment, the sequential compression chamber 506 can be surgically implanted in a patient. The sequential compression chamber 506 is positioned to surround a blood vessel, such that the compression sequence drives blood flow along a normal flow path. Shown in FIG. 5 is a sequential compression chamber 506 having four compression chambers 508A-D. As air is directed from outlet 504 and into chamber 508A, camber 508A compresses the blood vessel 510. Once chamber 508A compresses the blood vessel, air pressure is directed into the next chamber 508B. In one example, operation of chamber 508A can expose valves 509A or opening between chamber 508A and 508B allowing air to flow into the subsequent chamber. Air flow into chamber 508B causes chamber 508B to compress a corresponding section of the blood vessel 510. In some embodiments, as chamber 508A is compressed the blood vessel 510, the subsequent compression of the blood vessel by 508B forces blood flow along a desired flow path (e.g., 512). Typically, the sequential compression chamber is positioned to force blood flow along a normal flow path. Additionally, the compressed chamber 508A operates to prevent blood flow in a reverse direction.

Responsive to compression of 508B, chamber 508C is configured to compress the blood vessel 510. In some examples, the compression action of chamber 508B exposes valves 509B and allows air flow into the chamber 508C. Likewise compression of chamber 508C can trigger subsequent operation of the compression chamber 508D. The sequential compression of the chambers 508A-D propels blood flow in the direction of 512. In some embodiments, the chambers 508A-D can be configured to return to their non-compressive position once the compression cycle from 508A-D is complete. In further embodiments, the sequential compression chamber 506 cycles through compression and relaxation as a person breathes and air flow is directed from pressure chamber 502 through outlet 504 and into sequential compression chamber 506. In some embodiments, reduced air pressure can be achieved as a person exhales returning the pressure chamber to an at rest configuration, for example through a return vessel that directs air to the person's airway and/or to the pressure chamber (e.g., 502).

Figure 6:
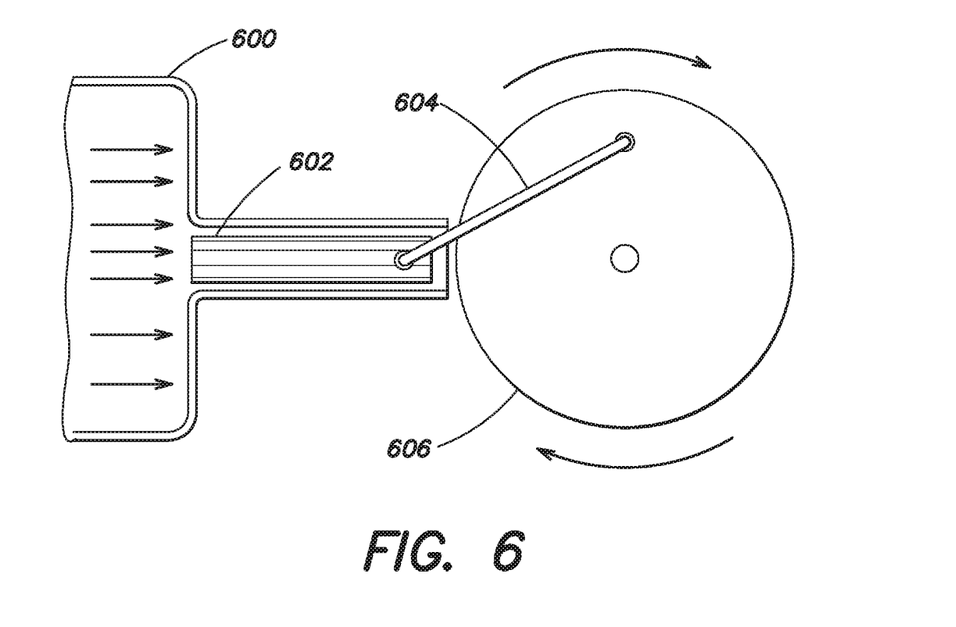
FIG. 6 is a partially transparent view of one embodiment of an air pressure bag connected to a piston.
Figure 7:
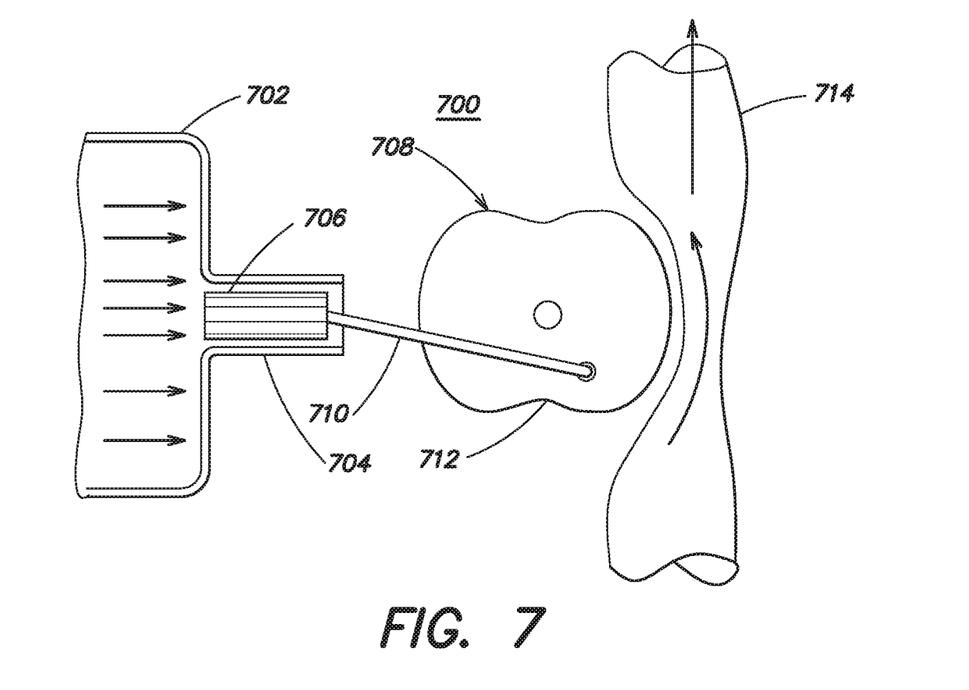
FIG. 7 is a partially transparent view of one embodiment of a piston and a flywheel.

In further embodiments, a pressure chamber 600 can be used to drive a piston 602, shown in FIG. 6. The pistconnected to a fly wheel 606 through a rod 604 or connector, rather than target a blood vessel. Operation of the piston via air pressure in the pressure chamber results in rotation of the fly wheel 606. In some embodiments, rotation of the fly wheel at 606 can be used to generate electricity. The electricity can in turn power conventional heart assist devices (e.g., pacemakers, etc.). In one alternative, the fly wheel can be positioned such that rotation of the fly wheel compresses a blood vessel directly, forcing blood flow to assist normal operation of the heart. Shown in FIG. 7 is an embodiment of a heart assist system 700. An air pressure chamber 700 collects air from normal breathing. Air pressure builds until released through outlet driving piston 706. Operation of the piston 706 can turn fly wheel 708 via rod or connector 710. In some embodiments, fly wheel 708 can be configured to have elliptical portions such that rotation of the wheel operates to compress and then release from a blood vessel 714, as fly wheel 708 rotates. In one example, the flywheel 708 is constructed and arranges with an asymmetrically configuration. The asymmetrical configuration can include one or more concave portions (e.g., 712), that are constructed and arranges to not act on an adjacent vessel 714 during rotation. Thus during rotation of the flywheel 708, the adjacent vessel 714 is compressed and released cyclically.

Figure 8A:
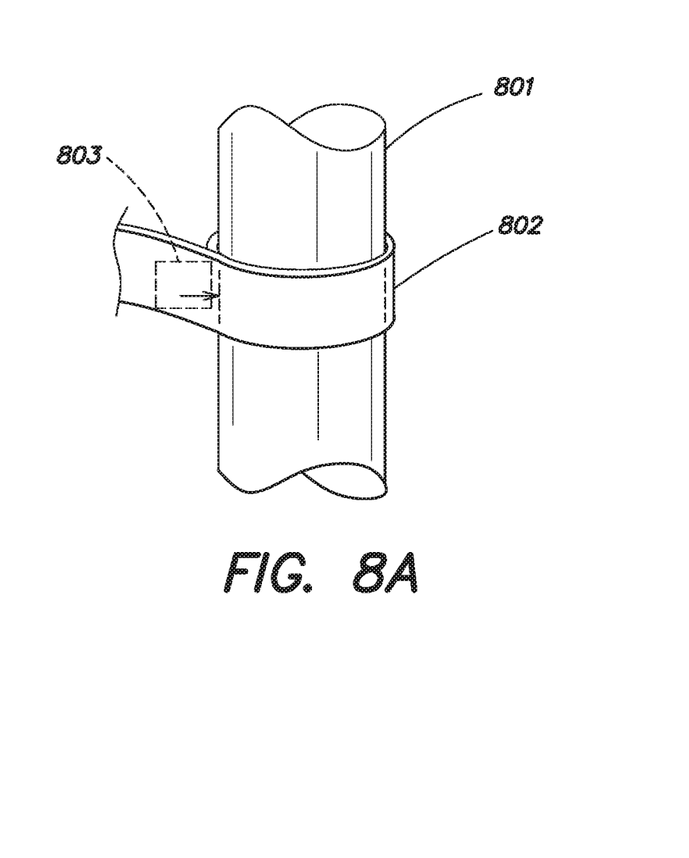
FIGS. 8A-8B illustrate additional components of some embodiments.
Figure 8B:
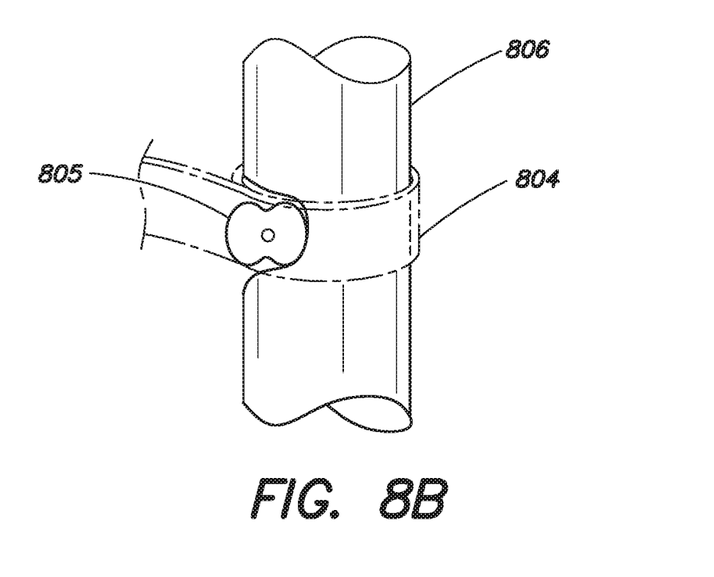

FIGS. 8A-B illustrate another embodiment having a collar component (e.g., 802 and 804). The collar component is constructed and arranged to wrap around an adjacent blood vessel to improve delivery of mechanical force to the vessel to assist blood flow. For example, in FIG. 8A piston 803 can exert maximal compression on the blood vessel 801 as the collar 802 holds the vessel 801 in place. Similarly operation of flywheel 805 can be improved by holding vessel 806 in place with collar 804. The collar components are optional, but can be incorporated into any embodiment to improve delivery of force to the blood vessel.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An implantable heart assist system, the system comprising:
   at least one air capture inlet;
   a pressure chamber;
   an actuator operative responsive to air pressure in the pressure chamber;
   one way flow valves disposed in the at least one air capture inlet;

wherein the actuator is positioned such that activation of the actuator compresses an adjacent blood vessel and forces blood flow; and wherein each air capture inlet of the at least one air capture inlet is adapted to be connected to an airway of a person.

2. The heart assist system according to claim 1, wherein the at least one air capture inlet permits air flow responsive to breathing by the person.

3. The heart assist system of claim 1, wherein the pressure chamber is connected to the at least one air capture inlet, and receives air flow from the at least one air capture inlet.

4. The heart assist system of claim 3, wherein the pressure chamber further comprises a releasably closed air outlet.

5. The heart assist system of claim 4, wherein the releasably closed air outlet is constructed and arranged such that the air outlet opens responsive to a threshold pressure or air volume.

6. The heart assist system of claim 4, wherein the releasably closed air outlet is connected to the actuator.

7. The heart assist system of claim 6, wherein the actuator is operated responsive to opening the releasably closed air outlet.

8. The heart assist system of claim 1, wherein the actuator further comprises a plurality of compression chambers.

9. The heart assist system of claim 8, wherein the plurality of compression chambers are constructed and arranged to sequentially actuate and compress the adjacent blood vessel.

10. The heart assist system of claim 9, wherein a respective one of the plurality of compression chambers includes a release valve connected to an adjacent one of the plurality of compression chambers.

11. The heart assist system of claim 10, wherein the release valve is constructed and arranged to be covered when the respective one of the plurality of compressions chambers is in a non-actuated state, and wherein the release valve is exposed responsive to actuation of the respective one of the plurality of compression chambers.

12. An implantable heart assist system, the system comprising:
  at least one air capture inlet;
  a pressure chamber;
  an actuator operative responsive to air pressure in the pressure chamber;
  wherein the actuator is positioned such that activation of the actuator compresses an adjacent blood vessel and forces blood flow;
  wherein the at least one air capture inlet comprises tapping tubing adapted to be mated to at least one internal breathing passage of a patient at a first end and connected to the pressure chamber at a second end.

13. The heart assist system according to claim 12, wherein the tapping tubing further comprises one way flow valves disposed in the tapping tubing.

14. An implantable heart assist system, the system comprising:
  at least one air capture inlet;
  a pressure chamber;
  an actuator operative responsive to air pressure in the pressure chamber;
  wherein the actuator is positioned such that activation of the actuator compresses an adjacent blood vessel and forces blood flow;
  wherein the actuator further comprises a piston, and the system further comprises a flywheel connected to the piston.

15. The heart assist system of claim 14, wherein the flywheel is positioned to compress the adjacent blood vessel responsive to rotation.

16. The heart assist system of claim 15, wherein the flywheel includes at least one concave portion such that upon rotation the concave portion releases the compression on the adjacent blood vessel.

* * * * *